(12) United States Patent
Blanchard

(10) Patent No.: US 9,808,430 B2
(45) Date of Patent: Nov. 7, 2017

(54) COMPOSITIONS AND METHODS RELATING TO RESVERATROL

(71) Applicant: Otis L. Blanchard, Austin, TX (US)

(72) Inventor: Otis L. Blanchard, Austin, TX (US)

(73) Assignee: WILMORE LABS LLC, San Antonio, TX (US)

( * ) Notice: Subject to any disclaimer, the term of this patent is extended or adjusted under 35 U.S.C. 154(b) by 0 days.

(21) Appl. No.: 14/691,320

(22) Filed: Apr. 20, 2015

(65) Prior Publication Data
US 2015/0216982 A1 Aug. 6, 2015

Related U.S. Application Data

(62) Division of application No. 12/955,810, filed on Nov. 29, 2010, now Pat. No. 9,125,858.

(60) Provisional application No. 61/265,035, filed on Nov. 30, 2009.

(51) Int. Cl.
*A61K 31/05* (2006.01)
*A61K 31/7004* (2006.01)
*A61K 47/26* (2006.01)
*A61K 9/28* (2006.01)
*A61K 9/00* (2006.01)

(52) U.S. Cl.
CPC .............. *A61K 31/05* (2013.01); *A61K 9/006* (2013.01); *A61K 9/0056* (2013.01); *A61K 47/26* (2013.01)

(58) Field of Classification Search
CPC .. A61K 9/0056; A61K 31/05; A61K 31/7004; A61K 47/26
USPC ........ 514/731, 733, 734, 736; 424/464, 465, 424/479
See application file for complete search history.

(56) References Cited

U.S. PATENT DOCUMENTS

| | | | |
|---|---|---|---|
| 2006/0014773 A1* | 1/2006 | McCleary | A23G 3/36 514/283 |
| 2006/0269616 A1* | 11/2006 | Giampapa | A23L 1/30 424/641 |
| 2007/0014833 A1* | 1/2007 | Milburn | A61K 31/05 424/427 |
| 2009/0175803 A1* | 7/2009 | Rubin | A23G 3/364 424/48 |

OTHER PUBLICATIONS

Peters, D. Medicated Lozenges. In: Lieberman HA, Lachman L, Schwartz JB, editors. Pharmaceutical Dosage Forms: Tablets. 2nd ed. New York: Marcel Dekker, Inc., 1989; p. 419-448.*

* cited by examiner

*Primary Examiner* — Irina Neagu
(74) *Attorney, Agent, or Firm* — Denise L. Mayfield; Husch Blackwell LLP

(57) ABSTRACT

The present invention relates to compositions and methods comprising resveratrol and uses thereof. Some embodiments include compositions and methods with increased bioavailability of resveratrol. Certain embodiments include compositions comprising resveratrol and a solubilizer. Particular embodiments include transmucosal delivery of resveratrol from the composition.

25 Claims, 5 Drawing Sheets

COMPOSITIONS AND METHODS RELATING TO RESVERATROL

CROSS-REFERENCE TO RELATED APPLICATIONS

The present application is a divisional of the U.S. patent application Ser. No. 12/955,810, filed Nov. 29, 2010. U.S. Ser. No. 12/955,810 is a utility application which claims priority to U.S. Provisional Patent Application 61/265,035, filed Nov. 30, 2009. The entire content of U.S. Ser. Nos. 61/265,035 and 12/955,810 is specifically incorporated herein by reference.

FIELD OF THE INVENTION

The present invention relates to compositions and methods comprising resveratrol and uses thereof. Some embodiments include compositions and methods with increased bioavailability of resveratrol. Certain embodiments include compositions comprising resveratrol and a solubilizer. Particular embodiments include transmucosal delivery of compositions.

BACKGROUND OF THE INVENTION

Resveratrol is a polyphenolic compound found in several plants. The compound includes double bonds and exists in two isoforms, trans-resveratrol and cis-resveratrol. The trans-isomer is the less stable form: trans to cis isomerization is facilitated by UV light and high pH, the cis to trans conversion is facilitated by low pH.

Resveratrol has extensive biological properties, including anticarcinogenic, anti-inflammatory, and estrogenic activities as well as cardiovascular protection, free-radical scavenging, inhibition/induction of apoptosis, and inhibition of platelet aggregation (See e.g., Mehdi S. et al., "Resveratrol addiction: To die or not to die." Mol. Nutr. Food Res. 2009, 53, 115-128; Baur J. et al., "Therapeutic potential of resveratrol: the in vivo evidence." Nature Reviews 5:493-506; and Ellen L. Robb and Jeffrey A. Stuart, "trans-Resveratrol as A Neuroprotectant," Molecules 2010, 15, 1196-1212, and references therein in each). For example, resveratrol has been shown to exhibit in vitro as well as in vivo chemopreventive and chemotherapeutic activities (Delmas, D., et al., "Resveratrol as a chemopreventive agent: A promising molecule for fighting cancer" Curr. Drug Targets 2006, 7, 423-442). Indeed, resveratrol has been shown to exhibit chemopreventive and chemotherapeutic activities in all three stages of carcinogenesis (i.e., initiation, promotion, and progression) (de la Lastra, C. A., Villegas, I., Resveratrol as an anti-inflammatory and anti-aging agent: Mechanisms and clinical implications, Mol. Nutr. Food Res. 2005, 49, 405-430). Chronic inflammation can lead to cancer, diabetes, and cardiovascular, pulmonary, and neurological diseases. One of the possible mechanisms for the protective activities of resveratrol is downregulation of inflammatory responses. Resveratrol has been shown to inhibit inflammatory responses through the inhibition of synthesis of various proinflammatory mediators, modulation of prostaglandin synthesis, and through the inhibition of factors such as IL-1β, NF-κB, and AP-1 (Das, S., et al., "Resveratrol: A therapeutic promise for cardiovascular diseases" Recent Patents Cardiovasc. Drug Discov. 2007, 2, 133-138). Resveratrol protects the cardiovascular system in a multidimensional way. One effect includes inhibition of apoptotic cell death at very low concentrations, thereby providing protection from various diseases including myocardial ischemic reperfusion injury, atherosclerosis, and ventricular arrhythmias.

In rodents, resveratrol is absorbed mainly in the duodenum; studies in rat intestine indicate that approximately 20% of available resveratrol is absorbed. In such studies, the majority of the absorbed resveratrol was detected in plasma as conjugated derivatives, while only a minute amount was detected in an unconjugated form. (Andlauer, W., et al., Assessment of resveratrol bioavailability in the perfused small intestine of the rat, Drugs Exp. Clin. Res. 2000, 26, 47-55). In humans, resveratrol is glucuronated in the liver and sulfated in both the liver and the duodenum (Aggarwal, B. B., et al., Role of resveratrol in prevention and therapy of cancer: Preclinical and clinical studies, Anticancer Res. 2004, 24, 2783-2840). The major derivatives of resveratrol glucuronidation are trans-resveratrol-3-O-glucuronide, trans-resveratrol-4'-O-glucuronide, and trans-resveratrol-3-O-sulfate (Yu, C.,. et al., Human, rat, and mouse metabolism of resveratrol, Pharm. Res. 2002, 19, 1907-1914). Kinetic analysis of resveratrol transformation suggests that, in the liver, glucuronidation is favored over sulfation, with similar rates of reaction.

In one study in humans, the bulk of an intravenous dose of resveratrol was converted to sulphate and gluconorated conjugates during absorption, (Walle, T., et al. High absorption but very low bioavailability of oral resveratrol in humans. Drug Metab. Dispos. 32, 1377-1382. (2004)). An analysis of plasma metabolites after oral dosing detected both sulphate and glucuronide conjugates. Five distinct metabolites were present in the urine, including, resveratrol monosulphate, two isomeric forms of resveratrol monoglucuronide, dihydroresveratrol monosulphate and dihydroresveratrol monoglucuronide. It is well known that modifications such as glucuronidation and sulphation reduce the cell permeability of small molecules and aid in their excretion. This extensive modification by the small intestine and liver during absorption greatly reduce the bioavailability of resveratrol.

SUMMARY OF THE INVENTION

The present invention relates to compositions and methods comprising resveratrol and uses thereof. Some embodiments include compositions and methods with increased bioavailability of resveratrol. Certain embodiments include compositions comprising resveratrol and a solubilizer. Particular embodiments include transmucosal delivery of compositions.

Some embodiments include methods of administering resveratrol to a subject. Some such methods include administering a solid or semi-solid pharmaceutical composition comprising resveratrol and a solubilizer, wherein the administering comprises the subject retaining the composition in its mouth for sufficient amount of time for oral transmucosal absorption of resveratrol.

In some embodiments, the solubilizer is selected from a co-solvent and a complexer. In some embodiments, the solubilizer comprises a sugar. In some embodiments, sugar comprises a monosaccharide. In some embodiments, the sugar is selected from the group consisting of ribose, 2-deoxyribose, deoxyribose, arabanose, ribulose, deoxyarabanose, xylose, deoxyxylose, fructose, deoxyfructose, and mixtures thereof. In some embodiments, the solubilizer comprises ribose. In some embodiments, the complexer comprises nicotinamide. In some embodiments, complexer forms a non-covalent stoichiometric association of two or more molecules with the resveratrol. In some embodiments, the co-solvent increases aqueous solubility of resveratrol by acting as a chaotrope and disrupting the molecular interactions of water. In sonic embodiments, the solubilizer comprises a sequestered hydrophobic region and a hydrophilic region.

In some embodiments, the resveratrol comprises trans-resveratrol.

In some embodiments, the composition is retained in the mouth for at least 5 minutes. In some embodiments, the composition is retained in the mouth for at least 10 minutes.

In some embodiments, the composition comprises a pH adjusting substance. In some embodiments, the pH adjusting substance comprises an acid. In some embodiments, the composition has an acidic pH.

In some embodiments, the solubilizer is in the range of about 2% to about 99% by weight of the composition.

In some embodiments, the administering comprises administering the composition via a route selected from the group consisting of bucal, sublingual, and gingival. In some embodiments, the administering comprises bucal administration. In some embodiments, the administering is comprises sublingual administration. In some embodiments, the administering is comprises gingival administration.

In some embodiments, the resveratrol is in the range from about 1% to about 50% by weight of the composition. In some embodiments, the solubilizer is in the range from about 5% to about 95% by weight of the composition.

In some embodiments, the subject is a mammal (e.g., a human).

In some embodiments, the composition comprises a dosage form selected from the group consisting of tablet, lozenge, semisolid lozenge, taffy, thin film, pressure capsule, and freeze dried solid. In some embodiments, the composition comprises a dosage form selected from the group consisting of taffy, tablet, lozenge, or thin film.

In some embodiments, the composition comprises about 5 mg to about 1000 mg resveratrol. In some embodiments, the composition has a weight of about 10 mg to about 5000 mg.

In some embodiments, the composition further comprises a coating, wherein the coating is impermeable to light.

In some embodiments, the composition enhances the stability of resveratrol to the trans isomer as compared to resveratrol without the solubilizer.

In some embodiments, the composition enhances the flavor of resveratrol in the composition as compared to resveratrol without the solubilizer.

In some embodiments, the administering is at least daily.

In some embodiments, the composition further comprises at least one additional component selected from the group consisting of coatings, sweeteners, thickeners, preservatives, colorings, flavorings, binders, cosmetic additives, and penetration enhancers. In some embodiments, the sweetener is selected from the group consisting of glucose, fructose, and tagatose. In some embodiments, the thickener is selected from the group consisting of polysaccharides, starches, vegetable gums, lectins, pectin, and proteins. In some embodiments, the preservative is selected from the group consisting of calcium propionate, sodium nitrate, sodium nitrite, sulfites disodium EDTA, butylated hydroxyanisole, and butylated hydroxytoluene. In some embodiments, the coloring is selected from the group consisting of E150, Annato E160b, E40, Betanin, Pandan, FD&C Blue No. 1, and FD&C Red No. 40. In some embodiments, the flavoring is selected from the group consisting of cinnamon, spearmint, and cherry. In some embodiments, the binder is selected from the group consisting of gum Arabic, gum tragacanth, gelatin, starch, dextrose, and mixtures thereof. In some embodiments, the cosmetic additive is selected from the group consisting of flavor crystals, and flavor maskers. In some embodiments, the penetration enhancer is selected from the group consisting of bile salts, surfactants, fatty acids, fatty acid derivatives, chelators, and chitosan.

In some embodiments, the composition comprises 100 mg resveratrol. in some embodiments, the administering achieves a serum $C_{max}$ of resveratrol greater than about 21 ng/ml. In some embodiments, the administering achieves an area under serum concentration (AUC) of resveratrol greater than about 19.5 ng*hr/ml.

In some embodiments, the administering achieves an improved bioavailability of the resveratrol compared to the bioavailability of resveratrol administered without the solubilizer. In some embodiments, the improved bioavailability comprises an increase in serum $C_{max}$ of resveratrol compared to the serum $C_{max}$ of resveratrol for resveratrol administered without the solubilizer. In some embodiments, the increase in serum $C_{max}$ is at least a 10%. In some embodiments, the increase in serum $C_{max}$ is at least 50% in some embodiments, the improved bioavailability comprises an increase in area under serum concentration (AUC) of resveratrol compared to the area under serum concentration (AUC) of resveratrol for resveratrol administered without the solubilizer. In some embodiments, the increase is at least 10%. In some embodiments, the increase is at least 50%.

In some embodiments, the resveratrol administered without the solubilizer lacks sulfertransferase or glucotransferase inhibitors. In sonic embodiments, the reserveratol administered without the solubilizer is administered with a pharmaceutically accepted drug release compound. In some embodiments, the pharmaceutically accepted drug release compound comprises a cyclodextrin. In some embodiments, the improved bioavailability is statistically significant.

In some embodiments, the amount of the resveratrol to the solubilizer is in the range of about 5 mg/g to about 500 mg/g. In some embodiments, the amount of the resveratrol to the solubilizer is in the range of about 20 mg/g to about 100 mg/g.

In addition to the foregoing methods, some embodiments include pharmaceutical compositions. Some such pharmaceutical compositions include resveratrol and a solubilizer in solid or semi-solid form.

In some embodiments, the solubilizer is selected from a co-solvent and a complexer. In some embodiments, the solubilizer comprises a sugar. In some embodiments, the sugar comprises a monosaccharide. In some embodiments, the sugar is selected from the group consisting of ribose, 2-deoxyribose, deoxyribose, arabanose, ribulose, deoxyarabanose, xylose, deoxyxylose, fructose, deoxyfructose, and mixtures thereof. In some embodiments, the solubilizer comprises ribose. In some embodiments, the complexer comprises nicotinamide. In some embodiments, the complexer forms a non-covalent stoichiometric association of two or more molecules with the resveratrol. In some embodiments, co-solvent increases aqueous solubility of resveratrol by acting as a chaotrope and disrupting the molecular interactions of water. In some embodiments, the solubilizer comprises a sequestered hydrophobic region and a hydrophilic region.

In some embodiments, the resveratrol comprises trans-resveratrol.

In some embodiments, the composition comprises a pH adjusting substance. In some embodiments, the pH adjusting substance comprises an acid. In some embodiments, the composition has an acidic pH.

In some embodiments, the percentage weight of the solubilizer is in the range of about 2% to about 99% of the composition. In some embodiments, the resveratrol comprises from about 1% to about 50% of the composition. In some embodiments, the solubilizer comprises about 5% to about 95% of the composition.

In some embodiments, the composition further comprises at least one additional component selected from the group consisting of coatings, sweeteners, thickeners, preservatives, colorings, flavorings, binders, cosmetic additives, and penetration enhancers. In some embodiments, the sweetener is selected from the group consisting of glucose, fructose, and tagatose. In some embodiments, the thickener is selected from the group consisting of polysaccharides, starches, vegetable gums, lectin, pectin, and proteins. In some embodiments, the preservative is selected from the group consisting of calcium propionate, sodium nitrate, sodium nitrite, sulfites disodium EDTA, butylated hydroxyanisole, and butylated hydroxytoluene. In some embodiments, the coloring is selected from the group consisting of E150, Annato E160b, E40, Betanin, Pandan, FD&C Blue No. 1, and FD&C Red No. 40. In some embodiments, the flavoring is selected from the group consisting of cinnamon, spearmint, and cherry. In some embodiments, the binder is selected from the group consisting of gum Arabic, gum tragacanth, gelatin, starch, dextrose, and mixtures thereof. In some embodiments, the cosmetic additive is selected from the group consisting of flavor crystals, and flavor maskers. In some embodiments, the penetration_enhancer is selected from the group consisting of bile salts, surfactants, fatty acids, fatty acid derivatives, chelators, and chitosan.

In some embodiments, the composition comprises at least about 100 mg resveratrol.

DETAILED DESCRIPTION

Figure 1:
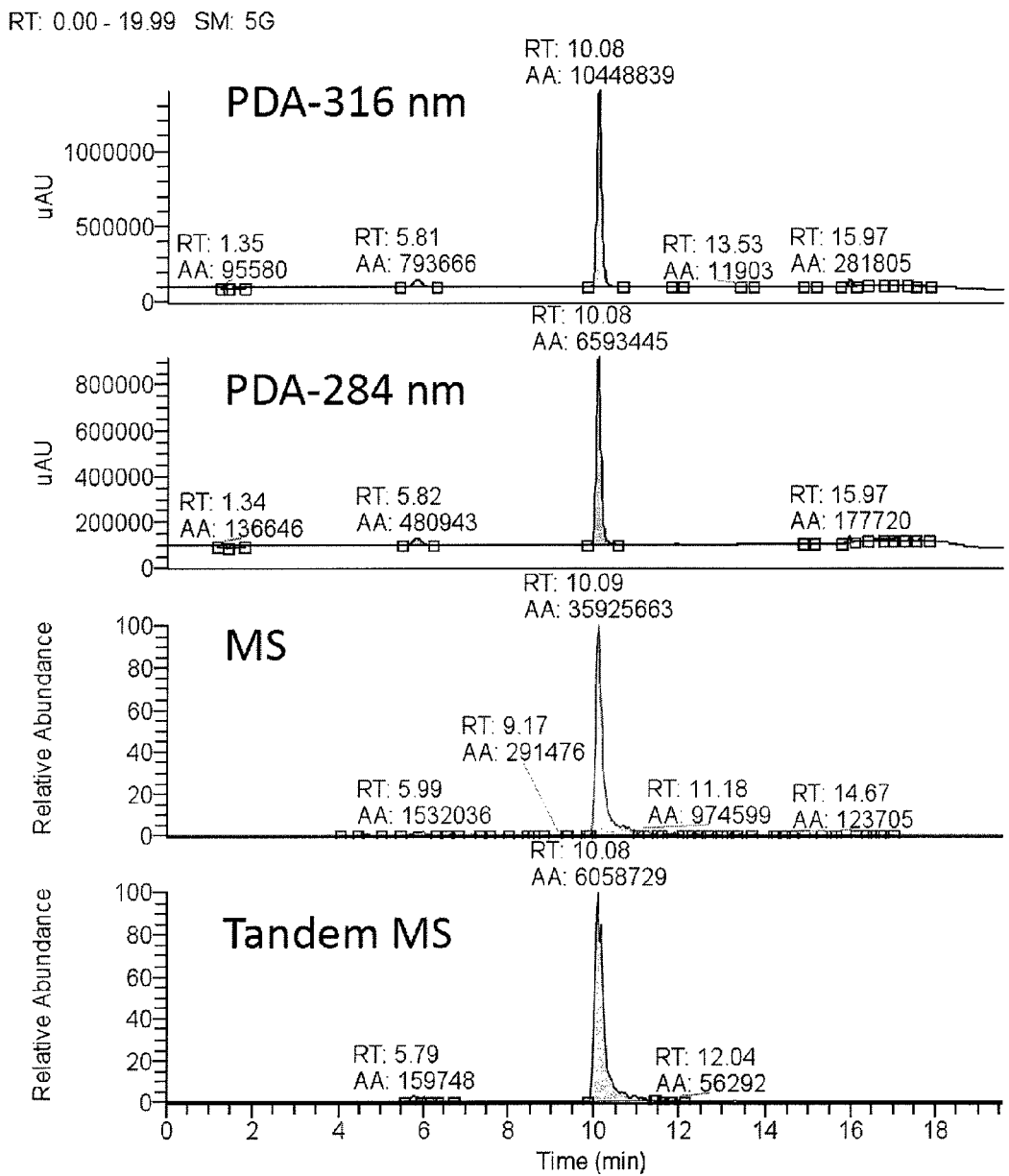
FIG. 1 shows U.V-HPLC and MS spectral traces for 1.6 mg resveratrol in 1 ml water. PDA-316 nm panel: trans isomer detected at peak, cis isomer is not detected (NL: 1.39E6; nm=315.5-316.5; PDA Avalon). PDA-284 nm panel: NL: 9.15E5; nm=283.5-284.5; PDA Avalon. MS Panel: NL: 2.8E6; m/z=226.60-227.60; F: -c APCI corona; sid=10.00 Full ms [100.00-1000.00] MS ICIS. Tandem MS panel: NL: 4.13E5; m/z=184.50-185.50; F: -c APCI corona; sid=10,00; Full ms2 227.00@cid45.00 [60.00-250.00] MS ICIS.
Figure 2:
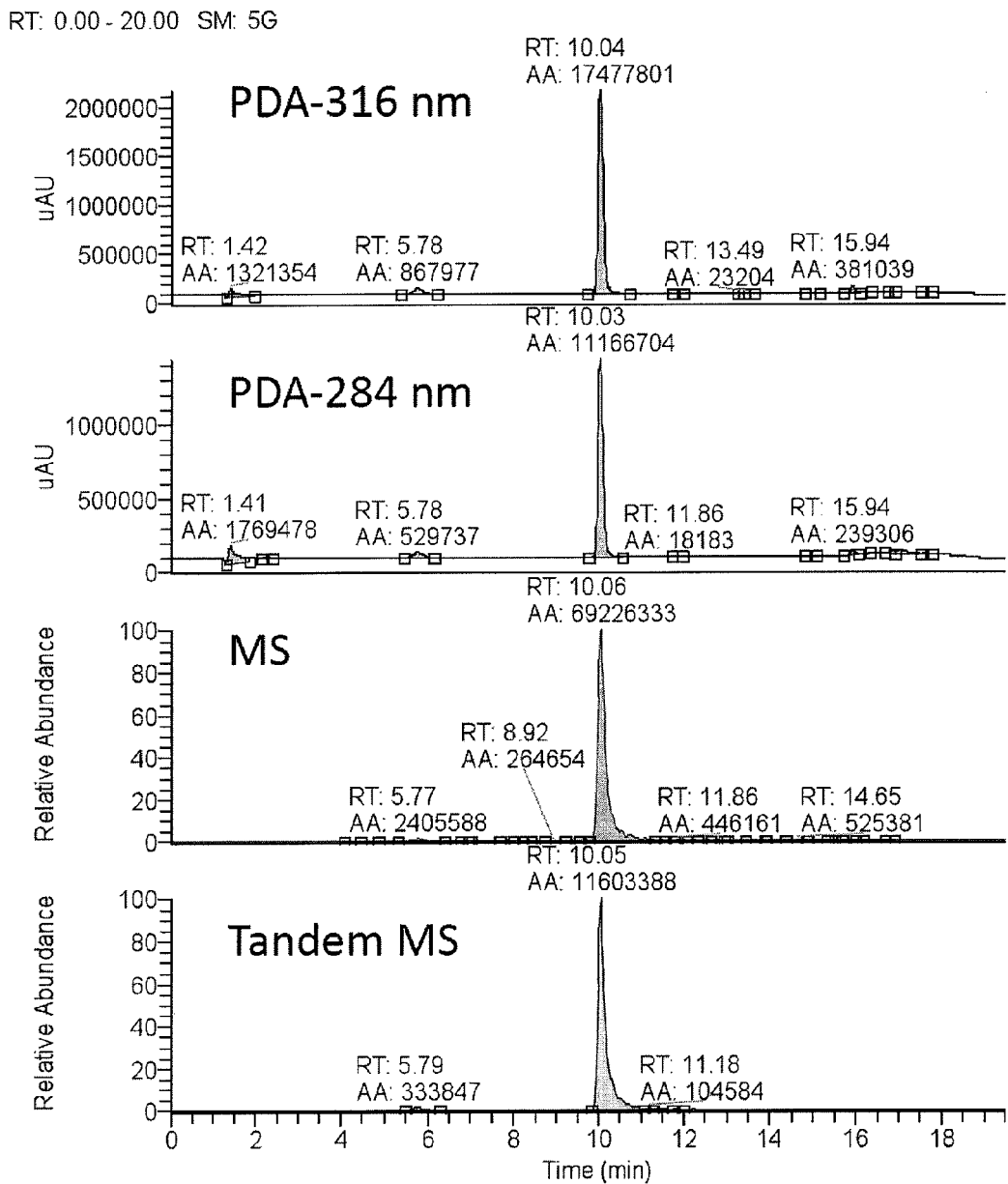
FIG. 2 shows U.V-HPLC and MS spectral traces for 1.6 mg resveratrol in 1 ml 3 M ribose. PDA-316 nm panel: trans isomer detected at peak, cis isomer is not detected. NL: 2.16E6; nm=315.5-316.5; PDA Avalon. PDA-284 nm panel: NL: 1.4.4E6; nm=283.5-284.5; PDA Avalon. MS Panel: NL: 5.17E6; m/z=226.60-227.60; F: -c APCI corona; sid=10.00 Full ms [100.00-1000.00] MS ICIS. Tandem MS panel: NL:8.96E5; m/z=184.50-185.50; F: -c APCI corona; sid=10.00; Full ms2 227.00@cid45.00 [60.00-250.00] MS ICIS.
Figure 3:
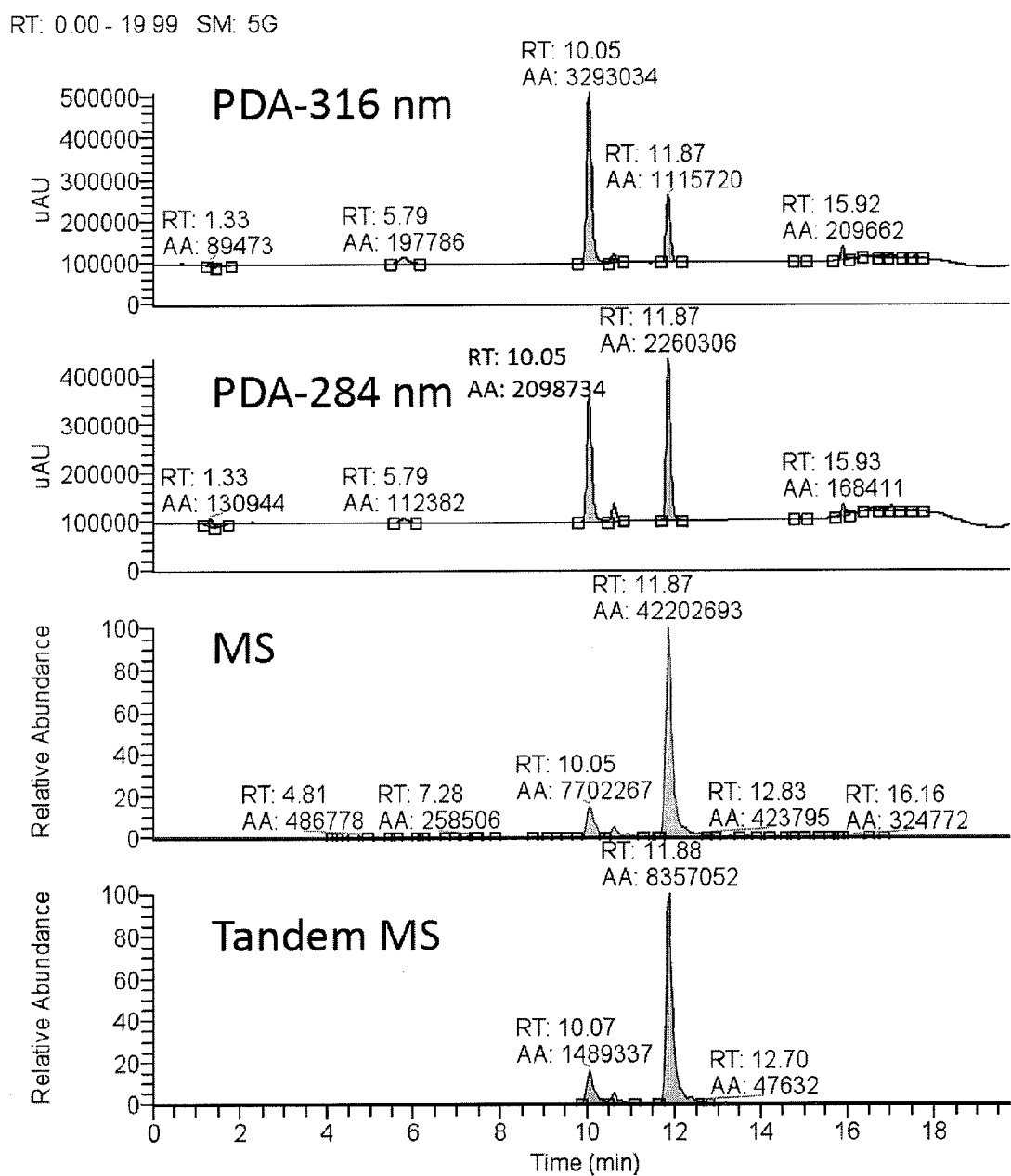
FIG. 3 shows U.V-HPLC and MS spectral traces for 1.6 mg resveratrol in 1 ml water exposed to U.V. light for 30 minutes. PDA-316 nm panel: trans isomer and cis isomer peaks detected; NL: 5.05E5; nm=315.5-316.5; PDA Avalon. PDA-284 nm panel: NL: 4.31E5; nm=283.5-284.5; PDA Avalon. MS Panel: NL: 3.90E6; m/z=226.60-227.60; F: -c APCI corona; sid=10.00; Full ms [100.00-1000.00] MS ICIS, Tandem MS panel: NL: 7.71E5; m/z=184.50-185.50; F: -c APCI corona; sid=10.00 Full ms2 227.00@cid45.00 [60.00-250.00] MS ICIS.
Figure 4:
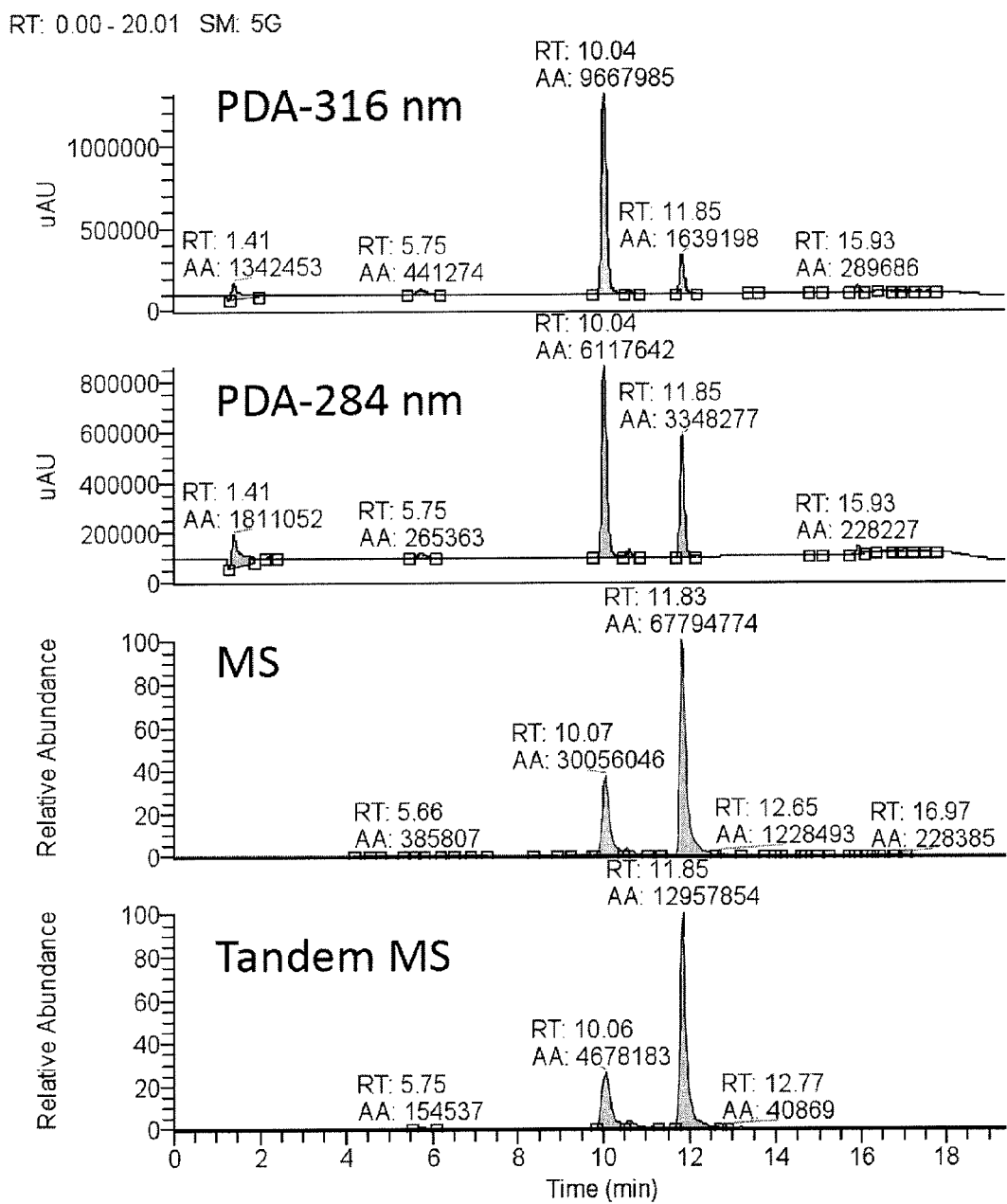
FIG. 4 shows U.V-HPLC and MS spectral traces for 1.6 mg resveratrol in 1 ml 3 M ribose exposed to U.V. light for 30 minutes. PDA-316 nm panel: trans isomer and cis isomer peaks detected. NL: 1.30E6; nm=315.5-316.5; PDA Avalon. PDA-284 nm panel: NL: 8.58E5; nm=283.5-284.5; PDA Avalon. MS Panel: NL: 6.51E6; m/z=226.60 227.60; F: -c APCI corona; sid=10.00 Full ms [100.00-1000.00] MS ICIS. Tandem MS panel: NL: 1.27E6; m/z=184.50-185.50; F: -c APCI corona; sid=10.00 Full ms2 227.00@cid45.00 [60.00-250.00] MS ICIS.

The present invention relates to compositions and methods comprising resveratrol and uses thereof. Some embodiments include compositions and methods with increased solubility of resveratrol. Some embodiments provided herein include methods for improving the bioavailability of resveratrol in a subject. Some embodiments include compositions and methods with improved peak plasma levels of resveratrol in the subject. Some methods include administering a composition comprising resveratrol and a solubilizer to the subject. In preferred embodiments, the administering comprises oral transmucosal delivery.

Certain compositions and methods provided herein can be used to administer resveratrol to a subject via the oral mucosal membranes achieving an increased bioavailability of the resveratrol. Certain compositions include a solubilizer. Some such solubilizers increase the aqueous solubility of resveratrol allowing for oral transmucosal absorption of the resveratrol via a subject's oral mucosal membranes. Accordingly, unconjugated resveratrol is absorbed directly into the bloodstream, without passing through the lining of the small intestines, and without being transported directly to the liver via the portal vein where it would also undergo extensive modification, sulfation and glucuronation, Certain Compositions Some compositions provided herein include resveratrol and/or analogs of resveratrol, An example structure of resveratrol is shown in formula (I):

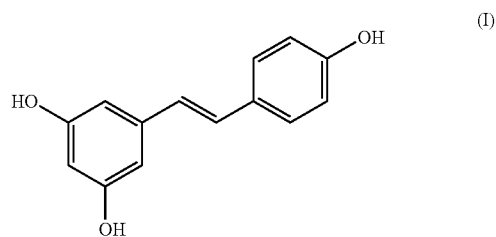 [SMILES: Oc1ccc(/C=C/c2cc(O)cc(O)c2)cc1]

Resveratrol (3,5,4'-trihydroxy-trans-stilbene) includes trans-resveratrol and cis-resveratrol. In some embodiments, trans-resveratrol is used.

Some compositions also include at least one solubilizer. As used herein, the term "solubilizer" means a compound that increases the aqueous solubility of another compound. Solubilizers include co-solvents and complexers. As used herein, the term "co-solvent" means a compound that increases the aqueous solubility of a compound by disrupting the molecular interactions of water. While not being bound by any particular theory, the disruption in the self-association of water leads to a reduction of its ability to squeeze out non-polar hydrophobic compounds, and consequently to the enhancement of the solubility of non-polar solutes. A co-solvent increases the aqueous solubility of a hydrophobic small molecule where a linear increase in solubilizer will increase aqueous solubility of a hydrophobic molecule in a logarithmic fashion. As used herein, the term "complexer" means a compound that increases the aqueous solubility of a second compound by associating with the second compound.

In some embodiments, a solubitizer comprises a sugar. Examples of sugars include monosaccharides, disaccharides, trisaccharides, oligosaccharides, and polysaccharides. In some embodiments, the monosaccharide is a pentose or furanose monosaccharide or deoxy-monosaccharide. In some embodiments, the monosaccharide is a hexose or pyranose monosaccharide. Example monosaccharides include glucose (dextrose), fructose, deoxyfructose, xylose, deoxyxylose, arabinose, deoxyarabanose, ribose, deoxyribose, 2-deoxyribose, ribulose, fucose, fuculose, rhamnose, tagatose, and derivatives thereof. Example disaccharides include as sucrose, lactose, maltose, trehalose, and derivatives thereof. Examples of polysaccharides include polydeoxyribose, starch, lignin, cellulose, and derivatives thereof. Sugars may also include sugar derivatives such as amino-sugars, methyl-sugars, and glycoproteins. Preferred sugars include ribose, 2-deoxyribose, deoxyribose, arabanose, ribulose, deoxyarabanose, xylose, deoxyxylose, fructose, deoxyfructose, and analogues thereof.

Some examples of co-solvents include water-miscible liquids. Such examples of co-solvents include ethanol, propylene, glycol, polyethylene glycol, glycerin, 2-pyrrolidone, N-methyl-2-pyrrolidone, and the like, More examples of solubilizers include complexers. Example of complexers include nicotinamide and cyclodextrins.

Without wishing to be bound to any one theory, in some embodiments, particular solubilizers, e.g., sugars, in the compositions and methods described herein promote the solubility of resveratrol and analogues thereof For example, some sugars enhance the solubility of certain hydrocarbons based on a co-solvent effect. Such co-solvent effects of sugars on the aqueous solubilities of hydrocarbons are described, for example, in Janado et al., (1985) "The Nature of the Co-solvent Effects of Sugars on the Aqueous Solubilities of Hydrocarbons." Bull. Chem. Soc. Jpn. 58:1913-1917, which is incorporated herein by reference in its entirety. Accordingly, in some embodiments, particular sugars and sugar derivatives are selected based on predicted solubilization properties. For example, in some embodiments, sugars having a hydrophobic region and a hydrophilic region are selected.

In some embodiments, particular complexers, e.g., nicotinamide, in the compositions and methods described herein promote the solubility of resveratrol and analogues thereof. Without wishing to be bound to any one theory, in some such embodiments, solubilization can include hydrotrophic solubilization can include stacking complexation; chaotrophy, i.e., the breakdown of water structure; or the formation of micellular aggregates. (Sanhvi et al., (2007) "Stacking complexation by nicotinamide: a useful way of enhancing drug solubility." Int. J. of Pharm. 336:35-41). Accordingly, in some embodiments, a complexer can be selected based on factors that include associations and interactions which increase aqueous solubility are also aMeted by aromaticity and molecular geometry.

In some embodiments, particular solubilizers, e.g., co-solvents, in the compositions and methods described herein promote the solubility of resveratrol and analogues thereof. Without wishing to be bound to any one theory, in some such embodiments, co-solvents increase aqueous solubility of hydrophobic molecules by disrupting hydrogen bonding lattice of water. The loglinear model is an example predictor of a solubilizer being a co-solvent where a linear increase in co-solvent in aqueous solution will increase solubility of a hydrophobic molecule in a logarithmic fashion. (Jain et al., (2007) "Solubilization of poorly soluble compounds using 2-pyrrolidone." Int. J. of Pharm. 342:1-5).

In certain embodiments, the resveratrolcompositions provided herein comprise a co-solvent system. Certain of such. co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, polyvinyl pyrrolidone. More example co-solvents include ethanol, propylene, glycol, polyethylene glycol, glycerin, 2-pyrrolidone, N-methyl-1-2-pyrrolidone, and the like.

As will be understood by one skilled in the art, a solubilizer can comprise the properties of both a complexer and a co-solvent. For example, 2-pyrrolidone and N-methyl-1-2-pyrrolidone can act as complexants at low concentrations and as co-solvents at high concentrations.

Nutraceutical and Pharmaceutical Compositions

In certain embodiments, the resveratrol compositions of the present embodiments may be prepared by including methods such as mixing, dissolving, granulating, dragee-making, levigating, emulsifying, encapsulating, entrapping or tabletting processes.

In certain embodiments, the resveratrol compositions provided herein are administered in the form of a dosage unit (e.g., lozenge, patch, gel, tablet, capsule, bolus, chewing gum, paste, etc.). in certain embodiments, such dosage units comprise a resveratrol composition provided herein, in a dose from about 1 µg/kg dose/body weight to about 50 mg/kg dose/body weight, and from about 2 µg/kg dose/body weight to about 25 mg/kg dose/body weight, from about 10 µg/kg dose/body weight to about 5 mg/kg dose/body weight. In certain embodiments, the nutraceutical and/or pharmaceutical agents provided herein are administered as needed. In certain embodiments, the nutraceutical and/or pharmaceutical agents provided herein are administered at least monthly, at least weekly, or at least daily. In some embodiments, the administering is at least once daily, at least twice daily, at least three times daily, at least four times daily. It is recognized by those skilled in the art that the particular dose, frequency, and duration of administration depends on a number of factors, including, the biological activity desired, the condition of the subject, and tolerance for the nutraceutical and/or pharmaceutical agent.

In preferred embodiments, the resveratro I compositions provided herein are prepared for buccal administration. Certain of such pharmaceutical agents are tablets or dosages formulated in conventional manner. In certain embodiments, a resveratrol composition is prepared for transmucosal administration. In certain of such embodiments penetrants appropriate to the barrier to be permeated are used in the formulation. Some such penetrants are generally known in the art. In more embodiments, the compositions provided herein are prepared for mucosal delivery. Routes of mucosal delivery are well known in the art.

In some embodim.ents, the resveratrol of certain compositions provided herein has increased permeability to oral epithelium, e.g., oral mucosal. membranes. In some such embodiments, adsorbtion and/or absorbtion of resveratrol in the oral cavity is increased. In some embodiments, the resveratrol of certain compositions provided herein is solubilized in a subject's saliva. In some such embodiments, adsorbtion to the surfaces in the oral cavity and/or absorbtion through the surfaces in the oral cavity of resveratrol is increased. In some embodiments, adsorption of resveratrol to the sub-mucosa and reticular layer of oral mucosa tissue and portions thereof are retained in the upper oral epithelium and basement membrane. In some embodiments, the resveratrol compositions provided herein further include mucoadhesive polymers to promote adsorption the mucosa.

In some embodiments, the resveratrol compositions provided herein comprise a resveratrol taste. In some such embodiments, the taste comprises a capsaicinoid or black pepper like taste In certain embodiments, a resveratrol composition provided herein is administered to a subject between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily oral transmucosal dosage regimen for a subject comprises a dose of between about 0.1 mg and about 5000 mg of resveratrol, about 5 mg and about 4000 mg, about 5 mg and about 3000 mg, about 5 mg and about 2000 mg, about 5 mg and about 1500 mg, about 10 mg and about 1000 mg, about 20 mg and about 500 mg, about 30 mg and about 200 mg, or about 40 mg and about 100 mg of a compound of the present embodiments. In certain embodiments, a daily dosage regimen is administered as a single daily dose. In certain embodiments, a daily dosage regimen is administered as two, three, four, or more than four doses.

Dosage amount, interval between doses, and duration of treatment may be adjusted to achieve a desired effect. In certain embodiments, dosage amount and interval between doses are adjusted to maintain a desired concentration of compound in a subject. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC).

In certain embodiments, certain resveratrol compositions provided may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In some embodiments, the composition contains stabilizers and preservatives are added to improve shelf live. Such stabilizers can include coatings to protect the core from degradation by light. In some embodiments, the compositions provided herein include a coating, sweetener, thickener, preservative, coloring, flavoring, binder, cosmetic additive, or penetration enhancer. Examples of sweeteners include glucose, fructose, tagatose, and commercially accepted sweeteners. Examples of thickeners include polysaccharides, starches, vegetable gums, lectins, pectin, or proteins. Examples of preservatives include calcium propionate, sodium nitrate, sodium nitrite, disodium BHA and BHT. Examples of colorings include E150, Annato E160b, E40, Betanin, Pandan, FD&C Blue No. 1, FD&C Red No. 40, etc. Examples of flavorings include cinnamon, spearmint, cherry, or other accepted flavorings. Examples of binders include gum Arabic, gum tragacanth, gelatin, starch, dextrose, or mixtures thereof. Examples of cosmetic additives include flavor crystals, flavor maskers, or other accepted methods. Examples of penetration enhancers include bile salts, surfactants, fatty acids and derivatives, chelators, and chitosan. In some embodiments, the compositions provided herein include a pH adjusting substance, e.g., an acid or a base. Some embodiments also including adding a coating to protect the resveratrol from light and preserve form.

Mucosal Delivery

Certain methods provided herein include mucosal delivery of particular compositions provided herein. Routes of mucosal delivery are well known in the art. Preferred methods include oral mucosal delivery. The oral cavity comprises the lips, cheek (buccal), tongue, hard palate, soft palate and floor of the mouth. The lining of the oral cavity is referred to as the oral mucosa, and includes the buccal, sublingual, gingival, palatal and labial mucosae. The mucosal tissues in the cheeks (buccal), the floor of the mouth (sublingual) and the ventral surface of the tongue account for about 60% of the oral mucosal surface area. The buccal and sublingual tissues are the primary focus for drug delivery via the oral mucosa because they are more permeable than the tissues in other regions of the mouth. The oral mucosa is highly vascularized, and therefore any of the compositions provided here diffusing into the oral mucosa membranes has direct access to the systemic circulation via capillaries and venous drainage. Thus, the compositions provided herein that are absorbed through the oral mucosa directly enter the systemic circulation, bypassing the gastrointestinal tract and first-pass metabolism in the liver.

Absorption via the oralmucosa is a passive diffusion process. By simplifying the oral mucosa into a hydrophobic membrane, Fick's first law can be used to describe the absorption process (equations 1 and 2):

$$P = \frac{D \cdot K_p}{h} \quad \text{(Equation 1)}$$

$$A = P \cdot C \cdot S \cdot t = \frac{D \cdot K_p}{h} \cdot C \cdot S \cdot t \quad \text{(Equation 2)}$$

where P is permeability coefficient, A is the amount of drug, ie. resveratrol, absorbed, D is the diffusion coefficient of the drug in the oral mucosa, Kp is the partition coefficient of the drug between delivery medium and the oral mucosa, h is the thickness of the oral mucosa, C is the free drug concentration in the delivery medium, S is the surface area of the delivery site on the oral mucosa and t is the duration of drug contacting the oral mucosa.

Parameters such as diffusion coefficient, partition coefficient and thickness of the tissue are inherent properties of the drug, e.g., resveratrol, and the mucosa. Other parameters, such as surface area, duration of drug delivery and concentration are controlled by the dosage form and formulation. As will be understood, free drug concentration is a consideration when developing transmucosal drug delivery dosage forms. The effective formulation advantageously releases the composition to the mucosal surface, with the drug, e.g., resveratrol, in its free form. If the drug is bound to other components in the formulation, it is not available for transmucosal delivery and the bioavailability will be greatly reduced.

Some compositions and methods provided herein include transmucosal delivery of drugs such as resveratrol with a variety of dosage forms. Examples of such dosage forms include tablets, lozenges (including lyophilized and bioadhesive), chewing gum, pastes, solution sprays, laminated systems and patches, hydrogels, adhesive films, hollow fibres, pressure capsules, taffy, freeze-dried solid, and microspheres.

Solid dose formulations can dissolve in the oral cavity, and generally, drugs are released and exposed to the entire mucosa and the top third of the oesophageal mucosa. In some embodiments, delivery of compositions provided herein can include administering the composition via a route including bucal, sublingual, and gingival routes.

Improved Bioavailability

Certain compositions comprising resveratroi or analogues thereof provided herein have improved bioavailabilit as compared to other compositions and/or routes of administration. in some embodiments, resveratrol compositions are advantageously administered by the oral transmucosal route. Without wishing to be bound to any one theory, such a route allow for greater peak plasma levels of unmodified resveratrol by circumventing first pass-metabolism in the small intestine and the liver. Other non-transmucosal routes of administration, such as oral delivery, result in resveratrol being metabolized in the small intestine and/or liver before the resulting metabolites of resveratrol enter the general circulation. Some embodiments of the compositions provided herein over further advantages by presenting resveratrol in a form that is rapidly absorbed in the oral mucosal membrane. In some embodiments, the compositions provided herein provide an increase in bioavailability from 0.1%-4% as compared to an oral dose or alternative formulation. Some embodiments include an increase of up to or exceeding 20% bioavailability.

In some embodiments, improved bioavailability includes an increased percentage of a dose that is absorbed by a subject. In some embodiments, improved bioavailability includes an increased period of time and/or a higher level of resveratrol that is present in serum as compared to an oral dose or alternative formulation. In some embodiments, improved bioavailability includes an increased period of time that resveratrol is present in serum at higher concentrations, for example, as the peak plasma level increases, then the area under plasma concentration (AUC) for resveratrol is increased as compared to an oral dose or alternative formulation. In some embodiments, resveratrol metabolites (e.g., resveratrol monoglucuronides, resveratrol-3-sulfate, and like) are produced at a later period of time after administration of resveratrol. For example, peak levels of resveratrol metabolites are produced in a subject at a later period after administration of resveratrol. In some embodiments, AUC values for resveratrol metabolites are decreased. In some embodiments, improved bioavailability includes an increased level of resveratrol in the serum of a subject, for example an increased $C_{max}$.

Methods for Improving Bioavailability of Resveratrol

Methods provided herein include methods for improving the bioavailability and peak plasma levels of resveratrol in a subject. Some such methods include administering a composition comprising resveratrol and a soluhilizer as described above to the subject. In preferred embodiments the administering comprises transmucosal delivery. In some preferred methods, the transmucosal delivery comprises oral transmucosal delivery.

In some methods for improving the bioavailability of resveratrol or analogue thereof in a subject, the administering achieves an area under serum concentration (AUC) of resveratrol greater than about 500 ng*hr/ml, greater than about 600 ng*hr/ml, greater than about 700 ng*hr/ml, greater than about 800 ng*hr/ml, greater than about 900 ng*hr/ml, greater than about 1000 ng*hr/ml, greater than about 1100 ng*hr/ml, greater than about 1200 ng*hr/ml, greater than about 1300 ng*hr/ml, greater than about 1400 ng*hr/ml, greater than about 1500 ng*hr/ml, greater than about 1600 ng*hr/ml, greater than about 1700 ng*hr/ml, greater than about 1800 ng*hr/ml, greater than about 1900 ng*hr/ml, greater than about 2000 ng*hr/ml, greater than about 2100 ng*hr/ml, greater than about 2200 ng*hr/ml, greater than about 2300 ng*hr/ml, greater than about 2400 ng*hr/ml, greater than about 2500 ng*hr/ml, greater than about 2600 ng*hr/ml, greater than about 2700 ng*hr/ml, greater than about 2800 ng*hr/ml, greater than about 2900 ng*hr/ml and greater than about 3000 ng*hr/ml. In some embodiments, the administering achieves an AUC greater than about greater than about 3500 ng*hr/ml, greater than about greater than about 4000 ng*hr/ml, greater than about greater than about 4500 ng*hr/ml, greater than about greater than about 5000 ng*hr/ml, greater than about greater than about 5500 ng*hr/ml, greater than about greater than about 6000 ng*hr/ml, greater than about greater than about 6500 ng*hr/ml, and greater than about greater than about 7000 ng*hr/ml, In some methods for improving the bioavailability of resveratrol or analogue thereof in a subject, the administering achieves a serum $C_{max}$ greater than about 20 ng/ml, greater than about 30 ng/ml, greater than about 40 ng/ml, greater than about 50 ng/ml, greater than about 60 ng/ml, greater than about 70 ng/ml, greater than about 80 ng/ml, greater than about 90 ng/ml, and greater than about 100 ng/ml. In some methods for improving the bioavailability of resveratrol or analogue thereof in a subject, the administering achieves a serum $C_{max}$ greater than about 100 ng/ml, greater than about 200 ng/ml, greater than about 300 ng/ml, greater than about 400 ng/ml, greater than about 500 ng/ml, greater than about 600 ng/ml, greater than about 700 ng/ml, greater than about 800 ng/ml, greater than about 900 ng/ml, and greater than about 1000 ng/ml. In some methods for improving the bioavailability of resveratrol or analogue thereof in a subject, the administering achieves a serum $C_{max}$ greater than about 1000 ng/ml, greater than about 2000 ng/ml, greater than about 3000 ng/ml, greater than about 4000 ng/ml, and greater than about 5000 ng/ml.

In some embodiments, the pharmacokinetic values described above may be achieved by using certain of the compositions and/or methods of delivery disclosed herein. For example, in one embodiment, improved AUC and/or improved $C_{max}$ are achieved by oral transmucosal delivery using a composition comprising a high concentration of resveratrol and a solubilizer as described above.

In some methods for improving the bioavailability of resveratrol in a subject, the amount of the resveratrol to solubilizer is in the range of about 5 mg/g to about 500 mg/g, about 20 mg/g to about 100 mg/g, 40 mg/g to about 80 mg/g, and 50 mg/g to about 70 mg/g.

In some methods for improving the bioavailability of resveratrol in a subject, the administering is at least monthly, at least weekly, or at least daily. In some embodiments, the administering is at least once daily, at least twice daily, at least three times daily, at least four times daily.

In some methods for improving the bioavailability of resveratrol in a subject, the dosage of the resveratrol is in the range of about 5 mg to about 10,000 mg or about 50 mg to about 5000 mg.

In some methods for improving the bioavailability of resveratrol in a subject, the final formulation size is in the range of 5 mg to about 10,000 mg or about 50 mg to about 5000 mg, In some methods for improving the bioavailability of resveratrol in a subject, the composition comprises, but is not limited to, a lozenge, chew, chewing gum, gel, taffy, paste, or patch.

Methods of Manufacture

The embodiments provided herein also relate to methods for dissolving resveratrol and its analogues for clinical application and dietary supplementation. In some methods for improving the bioavailability of resveratroi in a subject, the composition is prepared by a method comprising: providing as a base carrier, a high molar concentration of solubilizers in liquid form; and dissolving the resveratrol in the base carrier.

In some embodiments, in order to dissolve the resveratrol, high concentrations of a solubilizer mixture are utilized as a base. The solubilizer mixture can be in the form of syrup which is heated in order to dissolve the resveratrol. Dissolved levels may include 100 mg of resveratrol per gram of solubilizer syrup. From this solubilizerresveratrol mixture as a starting point, solutions may be prepared utilizing various sweeteners, binders, flavoring agents, coloring agents, preservatives, plant polysaccharides, disaccharides, emulsification agents, and/or oils, to optimize the soluhility. Alternatively, in some embodiments, no additives are used.

According to some such compositions and methods, resveratrol is incorporated into a base carrier for oral transmucosal delivery. A particularly preferred base carrier is made from a high molar concentration of solubilizer mixture in liquid form into which the resveratrol has been brought into aqueous solution and then solidified. The base carrier can be administered to the individual so that the individual retains the solubilizer mixture in the mouth, allowing for an increased amount of resveratrol to be absorbed through the mucous membranes of the mouth.

In some methods a composition is prepared by a method comprising: heating at least one solubilizer, to decrease its water content thereby forming a solid at room temperature; reheating the solid so produced to melt the solid and form a base carrier; and adding the resveratrol to the base carrier. In some embodiments, the solubilizer base is heated in an oven to about 90° C. for about 14 hours to decrease the water content of the syrup solubilizer base. In some embodiments, the heated syrup was approximately ⅕ water by weight and became solid at room temperature. In some embodiments, the solid was reheated to approximately 90° C. before adding the trans-resveratrol.

In some methods the composition is prepared by a method comprising: incorporating the resveratrol into a base carrier that requires chewing or retention in the mouth; the base carrier comprising a high molar concentration of at least one solubilizer in liquid form into which the resveratrol has been dissolved and later The embodiments provided herein also relate to methods for dissolving resveratrol and its analogues for clinical application and dietary supplementation. In order to dissolve the resveratrol, high concentrations of solubilizer is utilized as a base. The solubilizer mixture can be in the form of syrup which is heated in order to dissolve and incorporate the resveratrol. Dissolved levels may include 125 mg of resveratrol per gram of solubilizer syrup. From this solubilizerresveratrol mixture as a starting point, solutions may be prepared utilizing various sweeteners, binders, flavoring agents, coloring agents, and/or preservatives.

In some embodiments, the syrup is reheated to the point of solidifying, to thereby produce a solid composition that contains high levels of resveratrol. In some embodiments, the composition is coated. in some embodiments, a thickener is added to the formulation to assist in solubility and slow the dissolving of the formulation, and allowing for more absorption of the resveratrol in the mouth. in some embodiments, the formulation could also contains additives including but not limited to vitamin E, quercetin, or caffeine.

EXAMPLES

Example-Resveratrol and Fructose/Dextrose 20 g Fructose/Dextrose (90%/10%, m/m) syrup was incubated at about 90° C. for 14 hours. After incubation, the initial syrup had lost approximately ⅕ weight by water loss and became solid at room temperature. The solid was reheated to about 90° C. to melt the solid and the liquid syrup was allowed to cool. Resveratrol (500 mg 98% trans-resveratrol, capsules, Transmax™, Product No. 94922-73528) was added to the warm liquid syrup. The composition remained liquid and had a very light capsinoid or black pepper like taste.

A substance in a free form can elicit a taste through contact with the nerves and tissues of the mouth. Resveratrol has little or no taste when it is dry, dissolved in oil, or suspended in water. in a wet mouth, resveratrol has no taste. Surprisingly, when resveratrol was present in the fructosedextrose mixture, it had a distinct, strong, steady light capsaicinoid or black pepper like taste.

Example—Reservatrol and Ribose

A ribose/water solution (18 g/2 g) was heated. To the warm solution, resveratrol was added to achieve a final ratio of 100 mg resveratrol to 1000 mg solution. On cooling, the liquid provided a hot irritable sensation in the mouth of a subject, comparable to cinnamon, This data may show that solubility of resveratrol is increased in the presence of ribose.

Example—Resveratrol Solubility in Ribose

Resveratrol solutions were prepared and the solubility determined using methods that included LV. HPLC and mass spectrometry (See e.g., Boocock D, et al. Quantitation of trans-resveratrol and detection of its metabolites in human plasma and urine by high performance liquid chromatography, J Chromatogr B 2007;848:182-7). The solutions included 1.6 mg resveratrol in 1 ml water, 1.6 mg resveratrol in 1 ml 3 M ribose, 1.6 mg resveratrol in 1 ml water exposed to U.V. light for 30 minutes, and 1.6 mg resveratrol in 1 ml 3 M ribose exposed to U.V. light for 30 minutes. The peak areas of the LC traces using U.V. and MS spectral detection were determined. The percentage increase in the peak area with ribose (undiluted) sample was 83.1%. Table 1 summarizes the results.

TABLE 1

| Sample | Resveratrol UV | Resveratrol MS | Resveratrol MS/MS |
|---|---|---|---|
| 0.4 mg/ml standard in MeOH/water | 32589198 | 361620189 | 22825783 |
| 1.3 mg resveratrol in 1 ml water | 3757436 | 17991728 | 1055482 |
| 1.3 mg resveratrol in 1 ml 1M ribose | 6879044 | 34006422 | 2177343 |
| 1:1 dilution of water sample | 7414378 | 36350491 | 2235878 |
| 1:1 dilution of ribose sample | 10156011 | 59987321 | 4277049 |

Example—Solubility of Resveratrol 3M ribose

Resveratrol solutions were prepared and the solubility determined using methods that included U.V. HPLC and mass spectrometry. The solutions included 1.6 mg resveratrol in 1 ml water, 1.6 mg resveratrol in 1 ml 3 M ribose, 1.6 mg resveratrol in 1 ml water exposed to U.V. light for 30 minutes, and 1.6 mg resveratrol in 1 ml 3 M ribose exposed to U.V. light for 30 minutes. FIGS. 1-4 show U.V. and MS spectral traces for 1.6 mg resveratrol in 1 ml water, 1.6 mg resveratrol in 1 ml 3 M ribose, 1.6 mg resveratrol in 1 ml water exposed to U.V. light for 30 minutes, and 1.6 mg resveratrol in 1 ml 3 M ribose exposed to U.V. light for 30 minutes, respectively. Table 2 and 3 summarize the results.

TABLE 2

| Detection method | Water | 3M ribose | % increase |
|---|---|---|---|
| PDA (trans-316 nm, cis-284 nm) | 10448839 | 17477801 | 67.3 |
| Mass spectroscopy | 35925663 | 69226333 | 92.7 |
| Tandem mass spectroscopy | 6058729 | 11603388 | 91.5 |

TABLE 3

| Detection method | Water (UV exposed, trans) | Water (UV exposed, cis) | Ratio cis/trans | 3M ribose (UV exposed, trans) | 3M ribose (UV exposed, cis) | Ratio cis/trans |
|---|---|---|---|---|---|---|
| PDA (trans-316 nm, cis-284 nm) | 3293034 | 2260306 | 0.6864 | 9667985 | 3348277 | 0.3463 |
| Mass spectroscopy | 7702267 | 42202693 | 5.4793 | 30056046 | 67794774 | 2.2556 |
| Tandem mass spectroscopy | 1489337 | 8357052 | 5.6113 | 4678183 | 12957854 | 2.7698 |

Example—Pharmacokinetic Study

Subjects are administered 100 mg resveratrol by oral transmucosal administration of a resveratrol/solubilizer formulation (test), by oral administration of resveratrol/solubilizer mixture (control), or by oral transmucosal administration of a resveratrol/sucrose formulation (control). Resveratrol levels are measured in the serum and urine of the subjects at various intervals of time over a 24 hour period. Any adverse effects are recorded.

Resveratrol and its metabolites are extracted and separate using a gradient UV-high-performance liquid chromatography system (Boocock D, et al. "Quantitation of trans-resveratrol and detection of its metabolites in human plasma and urine by high performance liquid chromatography." J Chromatogr B 2007;848:182-7). Pharmacokinetic variables are determined (Boococket et al., (2007) "Phase I Dose Escalation Pharmacokinetic Study in Healthy Volunteers of Resveratrol, a Potential Cancer Chemopreventive Agent." Cancer Epidemiol Biomarkers Prev 16(6): 1246-1252). The following pharmacokinetic variables are calculated for resveratrol and its three major metabolites using a noncompartmentai pharmacokinetic approach and the "PhAST" (Phoenix Automated Statistics and Tabulation) validated proprietary software (MDS Pharma Services, 1999): area under the plasma concentration versus time curve (AUC; by the trapezoidal method), maximal plasma concentration ($C_{max}$) and time of maximal plasma concentration ($T_{max}$), average concentration over the total collection period ($C_{av}=AUC_{0-24}/24$ h), apparent elimination half-life ($ln2,k_{el}$, where $k_{el}$ is apparent elimination rate constant), apparent total clearance ($CL/F=dose/AUC_{inf}$), apparent renal clearance of resveratrol ($CL_R$; approximated by $Ae_{0-24}/AUC_{0-24}$, where $Ae_{0-24}$ is estimated total amount excreted in urine over the total collection period), and apparent volume of distribution of resveratrol [$V/F=dose(k_{el} \times AUC_{inf})$]. For a few subjects, pre-dose samples contain peaks coeluting with resveratrol or its metabolites. In these cases, AUC and $C_{max}$ values are adjusted assuming these peaks constituted pre-dose concentrations ($C_0$) of resveratrol or resveratrol metabolite. These adjustments are made using the formulas $AUC_{infcorr}=AUC_{infobs}-C_0/k_{el}$ and $C_{maxcorr}=C_{maxobs}-(C_0 \times e^{-kel \times T_{max}})$.

Results

Resveratrol administered with a resveratrol/solubilizer formulation by the oral transmucosal route achieves a greater peak plasma level and bioavailability than the oral transmucosal resveratrol/sucrose formulation (control) or the resveratrol/solubilizer formulation taken through the oral route (control).

Peak levels of resveratrol metabolites (e.g., resveratrol monoglucuronides and resveratrol-3-sulfate) in the serum of test subjects are initially detected at a lower level than peak levels of resveratrol metabolites in the serum of control subjects.

AUC values for resveratrol metabolites are lower in test subjects than AUC values for resveratrol metabolites in control subjects.

Serum $C_{max}$ levels of resveratrol are higher in test subjects than serum $C_{max}$ levels of resveratrol in control subjects.

Table 4 shows estimated pharmacokinetics of resveratrol and two metabolites that are predicted from the plasma of test and control subjects administered 100 mg resveratrol (Almeida, et al. (2009) "Pharmacokinetic safety profile of trans-resveratrol in a rising multiple-dose study in healthy volunteers." Mol Nutr Food Res. 53 Suppl 1:S7-15).

Figure 5:
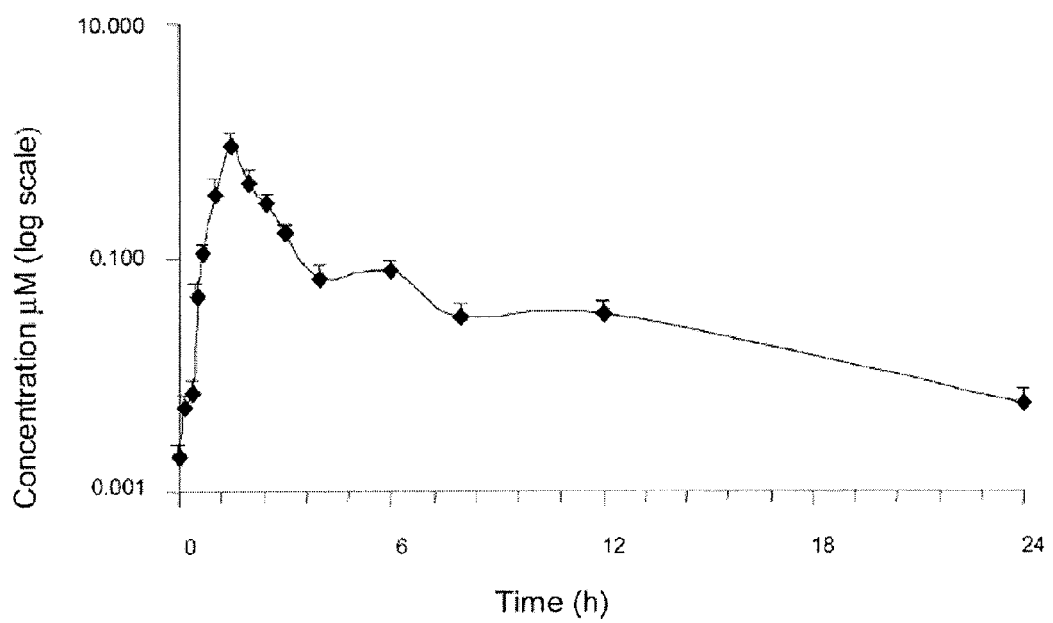
FIG. 5 shows a graph of an estimated time-concentration profile that is predicted for the serum concentration of resveratrol in subject administered a single oral dose of 1 g resveratrol.

FIG. 5 shows an estimated time-concentration profile of serum resveratrol concentration that is predicted in a subject administered 100 mg resveratrol by an oral route (Boocock et al., (2007) "Phase I Dose Escalation Pharmacokinetic Study in Healthy Volunteers of Resveratrol, a Potential Cancer Chemopreventive Agent." Cancer Epidemiol Biomarkers Prev 16:1246-1252).

TABLE 4

| | | Test | Control(s) |
|---|---|---|---|
| Resveratrol | $AUC_{inf}$ (ng*hr/ml) | 30 | 19.5 |
| | $C_{max}$ (ng/ml) | 50 | 21 |
| | $T_{max}$ (hr) | 0.3 | 1.3 |
| | $C_{av}$ (ng/ml) | 12 | 8 |
| | Half-life (hr) | 2.8 | 2.8 |
| Glucuronide 1 | $AUC_{inf}$ (ng*hr/ml) | 300 | 380 |
| | $C_{max}$ (mg/ml) | 70 | 80 |
| | $T_{max}$ (hr) | 3.5 | 2.0 |
| | $C_{av}$ (ng/ml) | 14 | 16 |
| | Half-life (hr) | 3.0 | 2.8 |
| 3-sulfate | $AUC_{inf}$ (ng*hr/ml) | 700 | 800 |
| | $C_{max}$ (mg/ml) | 150 | 227 |
| | $T_{max}$ (hr) | 3.0 | 1.5 |
| | $C_{av}$ (ng/ml) | 23 | 34 |
| | Half-life (hr) | 3.0 | 3.2 |

Comparative Example—Resveratrol and Sucrose

Resveratrol was added to a sucrose/water solution (1:1 v/v). The resveratrol failed to dissolve in the solution.

In another experiment, various sucrose/water mixtures were heated to boiling point. Reservatrol was added to each sucrose/water solution. On heating the mixtures to about 90° C., the mixtures formed thick yellow syrups, similar to mixtures of resveratrol and 90% fructose/10% dextrose m/m syrup. On cooling, resveratrol/sucrose/water mixtures formed crystalline solids composed of small crystals; in contrast, the sucrose/water solution formed a crystalline solid composed of large crystals. All resveratrol/sucrose/water mixtures failed to dissolve resveratrol in a similar fashion due to crystallization.

In another experiment, water was added to the solid resveratrol/sucrose/water mixtures. In each case the resveratrol precipitated out of solution.

These experiments demonstrate that resveratrol is not soluble in in the presence of all sugars. However, surprisingly, resveratrol was found to be soluble in ribose and in fructose/dextrose as exemplified above. These results demonstrate co-solvent sugars such as ribose can achieve surprising and superior results.

Comparative Example—Resveratrol and Dextrose

An aqueous solution of dextrose was prepared and heated to boiling. The resveratrol was added to the warm syrup and allowed to cool further. While still liquid, the syrup retained a capsinoid flavor. On cooling further, a white powdery mixture of crystals was formed. No capsinoid-like flavor was detected when the solid mixture was tasted.

This experiment further demonstrates that resveratrol is not well soluble in the presence of all sugars and the surprising and superior results obtained with co-solvent sugars Comparative Example—Resveratrol and Sugar Alcohols Resveratrol was added to warm solutions of xylitol or erythritol. The resveratrol was observed not to dissolve. On cooling the xylitol or erythritol solution formed a crystalline solid that appeared to exclude the resveratrol. No capsaicirioid-like flavor was detected when each reservatrol/xylitol and reservatrol/erythritol solid mixture was tasted.

Water was added to the each reservatrol/xylitol and reservatrol/erythritol mixture. However, in each case the resveratrol precipitated out of solution, These experiments demonstrate that resveratrol is not soluble in the presence of particular sugar alcohols. In contrast, superior results are obtained in the presence of co-solvent sugars such as ribose.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. The term "comprising" as used herein is synonymous with "including," "containing," or "characterized by," and is inclusive or open-ended and does not exclude additional, unrecited elements or method steps. All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all rnodifications and alternatives coming within th true scope and spirit of the invention.

What is claimed is:

1. A pharmaceutical composition in lozenge form consisting essentially of resveratrol and a solubilizer, wherein the solubilizer is selected from the group consisting of ribose and deoxyribose, wherein said pharmaceutical composition provides improved serum resveratrol bioavailability in a human subject upon administration compared to serum resveratrol bioavailability in a human subject upon administration of a pharmaceutical composition consisting essentially of resveratrol.

2. The pharmaceutical composition of claim 1 wherein the improved serum bioavailability of resveratrol is an increase in serum $C_{max}$ of resveratrol of at least 10% compared to the serum $C_{max}$ of resveratrol upon administration of a pharmaceutical composition consisting essentially of resveratrol without the solubilizer.

3. The pharmaceutical composition of claim 1, wherein the percentage weight of the solubilizer is about 2% to about 99% of the composition.

4. The pharmaceutical composition of claim 1, wherein the percentage weight of resveratrol is about 1% to about 50% of the composition.

5. The pharmaceutical composition of claim 1, wherein the lozenge is in a size suitable for buccal administration.

6. The pharmaceutical composition of claim 1, wherein the amount of resveratrol to solubilizer is about 5 mg/g to about 500 mg/g.

7. The pharmaceutical composition of claim 1, wherein the amount of resveratrol to solubilizer is about 50 mg/g to about 70 mg/g.

8. The pharmaceutical composition of claim 1, wherein the lozenge is a dosage form of about 50 mg to about 5000 mg resveratrol.

9. A pharmaceutical composition in lozenge form consisting essentially of resveratrol, a solubilizer, and a pharmaceutically acceptable carrier, wherein the solubilizer is selected from the group consisting of ribose and deoxyribose, wherein said pharmaceutical composition provides improved serum resveratrol bioavailability in a human subject upon administration compared to serum resveratrol bioavailability in a human subject upon administration of a pharmaceutical composition consisting essentially of resveratrol.

10. The pharmaceutical composition of claim 1, wherein the amount of resveratrol to solubilizer is about 100 mg/g to about 125 mg/g.

11. The pharmaceutical composition of claim 1, wherein said solubilizer is ribose.

12. The pharmaceutical composition of claim 1, wherein said deoxyribose is 2-deoxyribose.

13. A pharmaceutical composition in lozenge form consisting essentially of resveratrol, a solubilizer, and a pH adjusting substance, wherein the solubilizer is selected from the group consisting of ribose and deoxyribose, wherein said pharmaceutical composition provides improved serum resveratrol bioavailability in a human subject upon administration compared to serum resveratrol bioavailability in a human subject upon administration of a pharmaceutical composition consisting essentially of resveratrol.

14. The pharmaceutical composition of claim 1, wherein said solubilizer is from about 5% to about 95% by weight of said pharmaceutical composition.

15. The pharmaceutical composition of claim 1, wherein the percentage weight of resveratrol is about 1% of the pharmaceutical composition.

16. The pharmaceutical composition of claim 1, wherein the improved serum bioavailability is an increase in serum $C_{max}$ of resveratrol of at least 50% compared to the serum $C_{max}$ of resveratrol upon administration of a pharmaceutical composition consisting essentially of resveratrol.

17. A pharmaceutical composition in lozenge form consisting essentially of resveratrol, a solubilizer, and a binder, wherein the solubilizer is selected from the group consisting of ribose and deoxyribose, wherein said pharmaceutical composition provides improved serum resveratrol bioavailability in a human subject upon administration compared to serum resveratrol bioavailability in a human subject upon administration of a pharmaceutical composition consisting essentially of resveratrol.

18. The pharmaceutical composition of claim 1, further comprising a stabilizer.

19. The pharmaceutical composition of claim 1, further comprising a preservative.

20. The pharmaceutical composition of claim1, further comprising flavorings.

21. The pharmaceutical composition of claim 1, further comprising a thickener.

22. The pharmaceutical composition of claim 1, further comprising a coating.

23. A pharmaceutical composition in lozenge form consisting essentially of resveratrol, a solubilizer, and a penetration enhancer, wherein the solubilizer is selected from the group consisting of ribose and deoxyribose, wherein said pharmaceutical composition provides improved serum resveratrol bioavailability in a human subject upon administration compared to serum resveratrol bioavailability in a human subject upon administration of a pharmaceutical composition consisting essentially of resveratrol.

24. The pharmaceutical composition of claim 1 provided in a pack or dispenser device.

25. A pharmaceutical composition in a solid or semi-solid lozenge form consisting essentially of resveratrol and a solubilizer, wherein the solubilizer is selected from the group consisting of ribose and deoxyribose, wherein said pharmaceutical composition provides improved serum resveratrol bioavailability in a human subject upon administration compared to serum resveratrol bioavailability in a human subject upon administration of a pharmaceutical composition consisting essentially of resveratrol.

* * * * *